(12) United States Patent
Bone

(10) Patent No.: US 11,877,552 B2
(45) Date of Patent: Jan. 23, 2024

(54) METHOD FOR THE CULTIVATION, IDENTIFICATION, GRADING, AND PROCESSING OF CANNABINOID FREE HEMP MICROGREENS

(71) Applicant: Carlton Bone, Portland, OR (US)

(72) Inventor: Carlton Bone, Portland, OR (US)

( * ) Notice: Subject to any disclaimer, the term of this patent is extended or adjusted under 35 U.S.C. 154(b) by 49 days.

(21) Appl. No.: 17/786,335

(22) PCT Filed: Feb. 10, 2022

(86) PCT No.: PCT/US2022/015962
§ 371 (c)(1),
(2) Date: Jun. 16, 2022

(87) PCT Pub. No.: WO2022/173936
PCT Pub. Date: Aug. 18, 2022

(65) Prior Publication Data
US 2023/0210077 A1    Jul. 6, 2023

Related U.S. Application Data

(60) Provisional application No. 63/147,788, filed on Feb. 10, 2021.

(51) Int. Cl.
*A01H 6/28*      (2018.01)
*A01G 22/00*    (2018.01)
*A01H 5/12*      (2018.01)

(52) U.S. Cl.
CPC ............... *A01H 6/28* (2018.05); *A01G 22/00* (2018.02); *A01H 5/12* (2013.01)

(58) Field of Classification Search
CPC .......... A01G 17/00; A01G 22/00; A01H 6/28; A01H 5/10; A01H 5/12; A23L 5/20; A23L 35/00; G06K 9/00657
See application file for complete search history.

(56) References Cited

U.S. PATENT DOCUMENTS 11,179,757 B2 * 11/2021 Lee ........................... B09B 3/40
11,304,391 B1 *  4/2022 DeJong ................. A01G 7/045
(Continued)

FOREIGN PATENT DOCUMENTS

WO   WO-2013059500 A1 *  4/2013 ............... A01C 1/02
WO   WO-2018042445 A1 *  3/2018 ........... A01B 79/005
WO   WO-2019028542 A1 *  2/2019 ............... A01G 7/02

OTHER PUBLICATIONS

Mi et al. "Developing Production Guidelines for Baby Leaf Hemp (*Cannabis sativa* L.) as an Edible Salad Green; Cultivar, Sowing Density and Seed Size," Agriculture, Dec. 9, 2020 (Dec. 9, 2020), vol. 10, 617, pp. 1-16. entire document.

*Primary Examiner* — Ebony E Evans
(74) *Attorney, Agent, or Firm* — Mark C. Johnson; Johnson Dalal

(57) ABSTRACT

A method of grading and processing hemp microgreens into a consumable hemp microgreen desiccant that includes the steps of first screening a plurality of hemp seeds for a predetermined manufacturing use that is based on a plurality of quantitative seed characteristics, separating the plurality of hemp seeds into a first and a second separated plurality of hemp seeds based on at least one of a plurality of organoleptic seed characteristics predicated on a standard for manufacturing high-grade hemp microgreens, cultivating a plurality of hemp microgreens with the first separated plurality of hemp seeds, then screening the plurality of hemp microgreens based on the above-described organoleptic characteristics to confirm the plurality of hemp seeds maintain grading standards. Thereafter, the hemp microgreens are separated into high-grade and low-grade microgreens, packaging the high-grade hemp microgreens into a container for fresh sale, and processing the low-grade hemp microgreens into a consumable hemp microgreen desiccant.

12 Claims, 4 Drawing Sheets

(56) References Cited

U.S. PATENT DOCUMENTS

| | | | |
|---|---|---|---|
| 11,364,505 B2* | 6/2022 | Samburski | B02C 19/06 |
| 2014/0259920 A1* | 9/2014 | Wilson | A01G 7/045 |
| | | | 47/62 R |
| 2017/0223912 A1* | 8/2017 | Gagne | G01N 29/27 |
| 2018/0064055 A1 | 3/2018 | Lewis et al. | |
| 2018/0304274 A1 | 10/2018 | Bates | |
| 2019/0045720 A1* | 2/2019 | Archibald | B05B 7/32 |
| 2019/0191639 A1* | 6/2019 | Hegyi | A01G 9/20 |
| 2020/0327326 A1* | 10/2020 | Gavish | G06V 10/764 |
| 2020/0405685 A1 | 12/2020 | Lewis et al. | |
| 2022/0210981 A1* | 7/2022 | D'Acquisto | A01G 31/00 |

\* cited by examiner

METHOD FOR THE CULTIVATION, IDENTIFICATION, GRADING, AND PROCESSING OF CANNABINOID FREE HEMP MICROGREENS

FIELD OF THE INVENTION

The present invention relates generally to method and system of grading and processing hemp microgreens, a blend of juvenile plants and root material, into a shelf table consumable product, which provides for the improved processing techniques and technologies surrounding sprouting and curing hemp nutrients.

BACKGROUND OF THE INVENTION

Hemp seeds are generally well regarded as being extremely nutritious and nearly complete in terms of their nutritional profile. When these hemp seeds begin to spout, they generate or turn into hemp microgreens. Hemp microgreens are sprouted hemp seeds, which typically grow up to 10 cm height (or approximately 4 inches). Testing has shown that hemp microgreens can even be more nutritious than hemp seeds for many users because the sprouting process adds more nutrients.

The known processes and methods for grading and processing hemp microgreens fail to produce hemp microgreens with a standardized quality and effectiveness. Further, those known methods for grading and processing hemp microgreens are also very inefficient. Additionally, those known methods for grading and processing hemp microgreens do not maximize shelf stability.

Therefore, a need exists to overcome the problems with the prior art as discussed above.

SUMMARY OF THE INVENTION

The invention provides a method and system of effectively and efficiently grading and processing hemp microgreens that overcomes the hereinafore-mentioned disadvantages of the heretofore-known devices and methods of this general type.

With the foregoing and other objects in view, there is provided, in accordance with the invention, a method of grading and processing hemp microgreens into a consumable hemp microgreen desiccant that includes the steps of screening a plurality of hemp seeds for a predetermined manufacturing use that is based on a plurality of quantitative seed characteristics including a fatty acid profile, a cannabinoid and nutrient panel, and a projected detectible quantity of THC or CBD at any point during a plant's life cycle having a potential for a cannabinoid synthesis, separating the plurality of hemp seeds into a first separated plurality of hemp seeds and a second separated plurality of hemp seeds based on at least one of a plurality of organoleptic seed characteristics predicated on a standard for manufacturing high-grade hemp microgreens, cultivating a plurality of hemp microgreens with the first separated plurality of hemp seeds, screening the plurality of hemp microgreens based on organoleptic characteristics of the plurality of hemp microgreens and quantitative characteristics including a fatty acid profile and a cannabinoid and nutrient panel that measures for a total detectible quantity of cannabinoids, including THC or CBD, that are both cross referenced with the fatty acid profile and the projected detectible quantity of THC or CBD ascertained in the screening of the plurality of hemp seeds to maintain grading standards, separating the plurality of hemp microgreens into a first plurality of high-grade hemp microgreens based on the standard for manufacturing high-grade hemp microgreens and a second plurality of low-grade hemp microgreens, packaging the first plurality of high-grade hemp microgreens into a container for fresh sale, and processing the second plurality of low-grade hemp microgreens into a consumable hemp microgreen desiccant.

In accordance with a further feature of the present invention, the projected detectible quantity of THC or CBD is genetically screened to exclude any of the plurality of hemp seeds having the potential for the cannabinoid synthesis over the detectible quantity of THC or CBD at any point during the plant's life cycle.

In accordance with another feature, an embodiment of the present invention includes blending the consumable hemp microgreen desiccant and a hemp seed powder generated from the second separated plurality of hemp seeds to generate a homogenous consumable ingredient.

In accordance with yet another feature, an embodiment of the present invention also includes smashing the second separated plurality of hemp seeds into the hemp seed powder blended into the homogenous consumable ingredient.

In accordance with a further feature, an embodiment of the present invention also includes heat-treating the second separated plurality of hemp seeds before smashing into the hemp seed powder.

In accordance with an additional feature, an embodiment of the present invention also includes screening the plurality of hemp microgreens based on a quantitative characteristic that includes detecting the presence of mycotoxins and, when detected, not including said detected hemp microgreens with mycotoxins in the first and second separated plurality of hemp seeds.

In accordance with yet another feature, an embodiment of the present invention also includes the plurality of organoleptic seed characteristics formed by a seed size, a seed smell, a seed taste, a seed shape, and a seed shell integrity.

In accordance with an exemplary feature, an embodiment of the present invention also includes separating the plurality of hemp seeds having a seed size of approximately 0.3 mm and ascertaining a seed size standard deviation for categorizing a manufacturing use of the plurality of hemp seeds.

In accordance with an additional feature, an embodiment of the present invention also includes cleaning the plurality of hemp seeds based on the categorized manufacturing use and separating a plurality of hemp seeds into a third separated plurality of hemp seeds based on the manufacturing use.

In accordance with yet another feature, an embodiment of the present invention also includes randomly screening the plurality of hemp seeds for a predetermined manufacturing use.

In accordance with a further feature of the present invention, the detectible quantity of THC or CBD at any point during a plant's life cycle is 0.001%.

Although the invention is illustrated and described herein as embodied in a method and system of grading and processing hemp microgreens, it is, nevertheless, not intended to be limited to the details shown because various modifications and structural changes may be made therein without departing from the spirit of the invention. Additionally, well-known elements of exemplary embodiments of the invention will not be described in detail or will be omitted so as not to obscure the relevant details of the invention.

It is to be understood that the disclosed embodiments herein are merely exemplary of the invention, which can be embodied in various forms. Therefore, specific structural and functional details disclosed herein are not to be interpreted as limiting, but merely as a basis for future claims and as a representative basis for teaching one of ordinary skill in the art to variously employ the present invention in virtually any appropriately detailed structure. Further, the terms and phrases used herein are not intended to be limiting; but rather, to provide an understandable description of the invention. It is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION OF INVENTION

Figure 1:
FIG. 1 depicts an overhead view of graded and sorted microgreens awaiting further processing, wherein the high grade microgreens are depicted in the bottom right have been trimmed, while the remaining images depict low-grade microgreens that have been plucked and have not received trimming in accordance with one embodiment of the present invention.

The invention described herein provides a method and system of grading and processing hemp microgreens that overcomes known disadvantages of those known devices and methods of this general type. In light of the known methods and systems, it would be desirable to have a process for processing hemp microgreens that standardizes quality, while current methods of sprouting hemp may be able to create a similar product, the difference between sprouts and microgreens is directly addressed in this process. Furthermore, it would be desirable to have a process that maximizes shelf stability of these products. Still, further, it would also be desirable to have a process for nutritional availability and palatability. The disclosed process advantageously fills these needs and addresses the aforementioned deficiencies by providing a process to grade and process hemp microgreen desiccant into consumable goods that goes beyond existing sprouting techniques.

The attached figures are incorporated in and form part of the specification, and serve to further illustrate various embodiments and explain various principles and advantages all in accordance with the present invention. Moreover, it is believed that the invention will be better understood from a consideration of the following description in conjunction with the drawing figures, in which like reference numerals are carried forward.

Generally, the present invention relates to a method of grading and processing hemp microgreens, a blend of juvenile plants and root material into a shelf table consumable product, which provides for the improved processing techniques and technologies surrounding sprouting and curing hemp nutrients. In order to carry out this method, the following core steps are followed: Upon cultivating hemp seeds for ten (10) days in a soil medium, at which time the resulting microgreens are graded and harvested using specific and proprietary criteria to distinguish between high and low grade greens, greens are then processing accordingly with low grade greens being thermally dehydrated then manually pulverized, or juiced and dehydrated with a food-safe chemical desiccant while high grade greens will be juiced and freeze-dried, the result products will be screened for bacteria, pathogens, residual solvents, and moisture; final processing steps include blending with other ingredients, and or packaging for sale and consumption. Ultimately, at the conclusion of these steps, a desiccant is produced from hemp microgreens which can be consumed directly, utilized as a stand-alone nutrient or food ingredient, or further incorporated into a dietary supplement.

Figure 2:
FIG. 2 depicts a perspective view of desiccated and pulverized low grade microgreens in accordance with one embodiment of the present invention.
Figure 3:
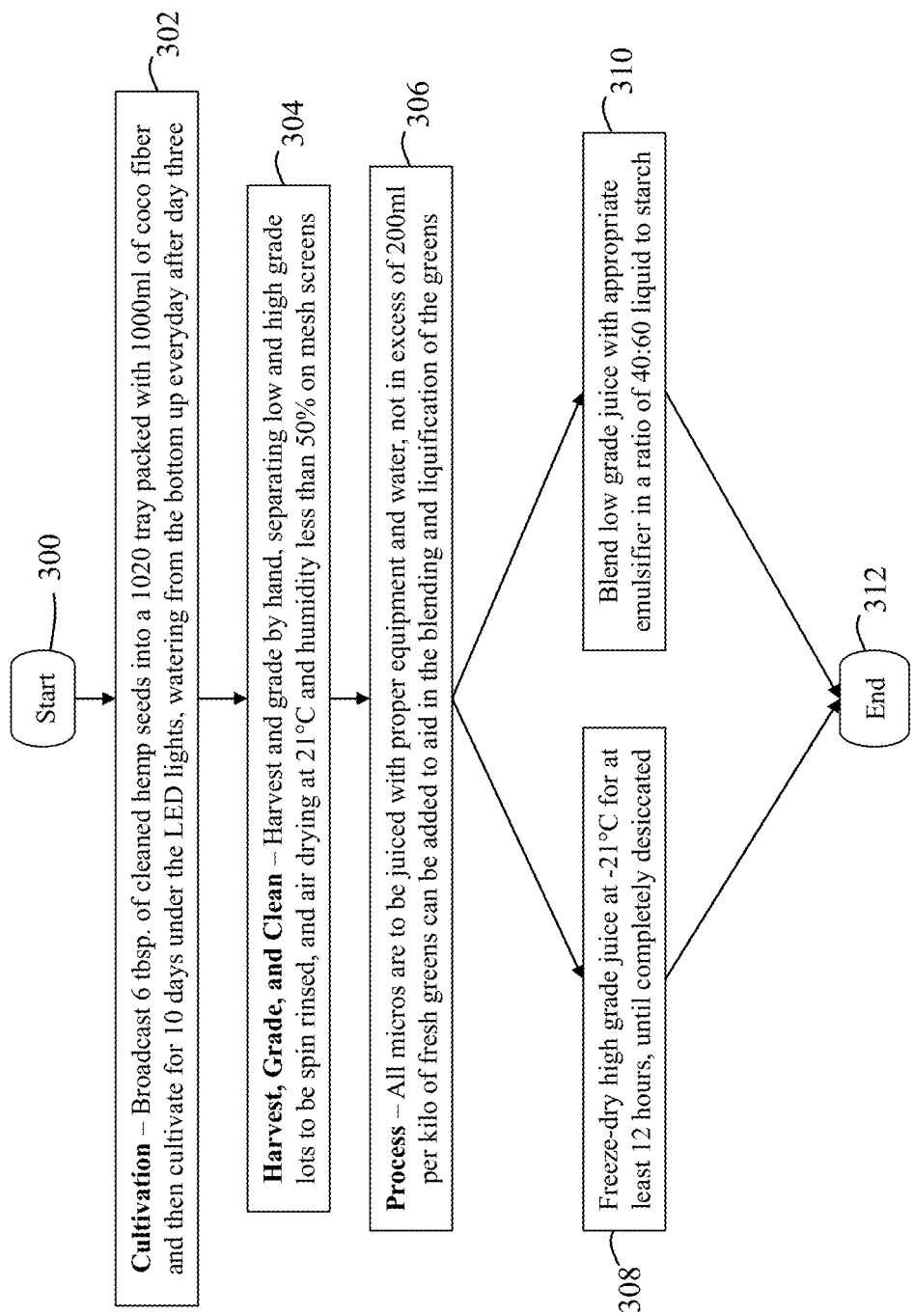
FIG. 3 is a process flow diagram depicting the basic steps from cultivation to processing as it relates to growing hemp microgreens and manufacturing hemp microgreen desiccant in accordance with one embodiment of the present invention.

Referring now to FIGS. 1-3, various views depicting photos and/or steps of grading and processing hemp microgreens in accordance with embodiments of the present invention are shown. Although the figures show several advantageous features of the present invention, the invention can be provided in several shapes, sizes, combinations of features and components, and varying numbers and functions of the components. The method and system of grading and processing hemp microgreens can be described as generally includes the steps of cultivating and processing hemp microgreens for standardized quality. Specifically, the hemp microgreens include a blend of juvenile sprouts and roots into a shelf table consumable product, which provides for the improved cultivation techniques and technologies surrounding sprouting and curing of hemp nutrients. In order to carry out this method, the following steps may be followed: Start by cleaning and treating the hemp seeds; followed by germinating the seeds before cultivating them hydroponically; upon sprouting, harvest crops, separating for quality according to grading criteria as well as testing lots for bacteria, pathogens, residual solvents, and moisture; final processing steps include either curing, blending, and or milling. Ultimately, at the conclusion of these steps, a desiccant is produced from hemp microgreens which can be consumed directly, as a stand-alone nutrient or food ingredient, or further incorporated into dietary supplement.

Said another way, the method and system of grading and processing hemp microgreens includes the steps of cultivating a plurality of hemp microgreens, grading and harvesting the plurality of hemp microgreens into either a high grade or a low grade, and processing the high grade or the low grade plurality of hemp microgreens into a consumable hemp microgreen desiccant.

In one embodiment, the inventive process can be described as cultivating hemp microgreens for approximately ten days in a tray with a soil medium in a temperature-controlled and humidity controlled environment, watering as appropriate. Next, the process may include, harvesting the microgreens, preferably when the following conditions are met: (1) Visually: Stemmy green sprout (approximately 5-10 cm) with cotyledons, one pair of true leaves (approximately 2 cm) with a single point, and some budding for new growth. Slight fuzziness on true leaves, sawed. Thin whitish green or red stem, (approximately 2-3 mm) and thinner tap root (approximately <1 mm) with some ancillary root expression up to approximately 15 cm in length; (2) Sensory: Slight fuzziness on true leaves, and crisp and slightly fibrous stem, snappable; (3) Smell: Grassy; and/or (4) Taste: Bitter and slightly peppery, faint citrus finish, wherein a mouthfeel is similar to oregano and tastes comparable to arugula microgreens.

With reference to FIG. 1, the plurality of microgreens are subject to two quality inspection touchpoints from harvesting to final packaging. The first step involves grading individual trays for high and low grade greens before individually grading the greens. Grading criteria for high and low grade micros is as follows: (1) High Grade: A straight, 4-6 cm green or red stem with symmetrical leaves and even color without blemishes. Seed hull should have completely fallen from the sprout and only four leaves (two true and two cotyledons) should be visible; (2) Low Grade: Any single criteria renders a sprout Low Grade, while any High Grade greens damaged during harvest or handling become Low Grade: (a) Retention of seed or husk in part or whole, or residue from the seed and husk, (b) Improper opening manifested as asymmetrical, uneven growth or unfurled and misshapen leaves (cotyledons and true leaves). Sprouts with two sets of partially mature or mature true leaves are also considered low grade sprouts, however some budding does not, (c) Nutrient deficiencies, specifically, yellowing in the leaves or excessive whiteness in the stems, (d) Stem length in excess of 6 cm or that is curved or bent.

In one embodiment, trays are screened for a ratio of high and low grade with a visual inspection. Trays with a ratio of 70:30 (High to Low Grade) or greater (meaning a higher percentage of high grade greens) will be separated for trim harvesting, the remaining trays will be pulled and harvested before being cleaned and prepared for further harvesting. In another embodiment, trays separated for pluck harvesting are pulled in a manner that maximizes root retention and rinsed before being left to air dry. Trays being trimmed are to be cut in a manner that maximally preserves the quality of the greens. This process involves gently grabbing a group of micros by the leaves to reveal the stem at an angle, before cutting near the soil line while softly pulling. In another embodiment, during harvest, low grade micros will be separated manually. High grade greens that will not be further processed are then cleaned, and given a final quality assessment while being packaged, which involves batch testing for bacteria, moisture content, and toxins.

Further, an additional step includes processing the plurality of microgreens within approximately twelve (12) hours of harvesting, after being graded, sorted, and cleaned. Low Grade greens are processed in one of two ways; manually and chemically, while High Grade greens are to be juiced and then freeze dried and are able to be used for further research analysis, chemical extraction, or packaging for human consumption. Next, another steps includes manually processing the microgreens by thermal desiccation of greens with a dehydrator before being pulverized into a powder which is suitable for blending or standalone consumption.

Further, with reference to FIG. 2, an additional steps includes chemically processing by starting with juicing before desiccation involving a food safe additive, typically a combination of arrowroot starch and gum arabica, in order to achieve microencapsulation of the liquid. This process extends to and covers a variety of methods of lyophilization not explicitly mentioned herein. The result of this process is a shelf-stable ingredient fit for blending or standalone consumption. FIG. 2 depicts desiccated and pulverized Low Grade microgreens.

The present invention can also be described as carrying out one or more of the following steps: (1) blending Low-grade hemp microgreen desiccant with green tea (matcha) as well as assorted aromatics (lemon verbena, citrus peel, etc.) and subsequently steeped then whisked in hot water to create a flavored beverage, (2) spraying High-grade hemp microgreen desiccant with green tea (matcha) extract as well as botanically derived terpenes (limonene, Humulene, etc.) and subsequently steeped then whisked in hot water to create a flavored tea beverage, (3) blending desiccated greens of both grades with nutrients such as vitamins, minerals, and proteins to create a supplement similar to existing greens powders, (4) introducing high-grade desiccant, and harvested and graded biomass may to appropriate closed-loop extraction systems [e.g. as described in U.S. Pat. No. 6,403,126, which is incorporated herein by reference] to afford for the concentration, extraction, and isolation of various compounds (Cannflavins, tri-terpenoids, etc.) for use.

Figure 4:
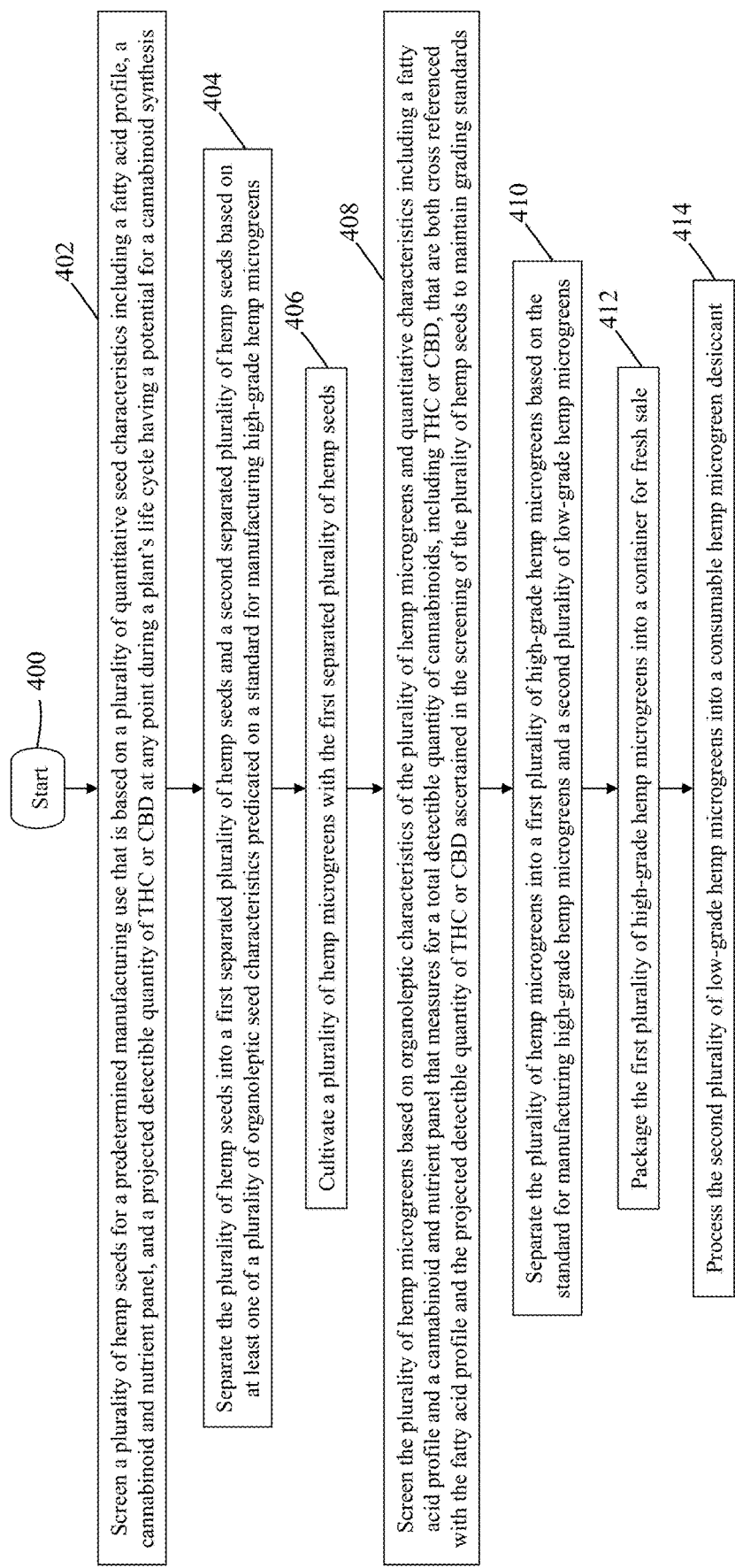
FIG. 4 is a process flow diagram depicting a method of grading and processing hemp microgreens into a consumable hemp microgreen desiccant in accordance with one embodiment of the present invention.

With reference to process flow diagram depicted in FIG. 3, the present invention can also be described as starting at step 300 and then proceed to step 302 of cultivating hemp microgreens, then proceeding to the step 304 of grading and harvesting microgreens, grading harvested microgreens into low and high lots and processing accordingly, and/or utilizing desiccated micro greens as a food ingredient, or supplement, or standalone consumption. Although FIG. 3 and FIG. 4 show a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIGS. 3-4 for the sake of brevity. In some embodiments, some or all of the process steps included in FIGS. 3-4 can be combined into a single process.

Currently, there are a number of solutions for sprouting hemp seeds. Some of these solutions attempt to create agricultural grade products, but these solutions fail to meet the needs of the industry because of their scalability and their lack of applicability to microgreens as opposed to sprouts. Other solutions attempt to encourage consumers to self-sprout, but these solutions are similarly unable to meet the needs of the industry because of the lack of quality control metrics that address the differences between sprouts and microgreens. Still, other solutions seek to create best practices for consuming hemp, there is little guidance on how to process fresh greens into consumable products or for further research and analysis.

The disclosed method and system are unique when compared with other known processes and solutions in that it provides (1) a standard method and process; (2) quality control metrics; and (3) a method for shelf-stable storage of processed materials. The disclosed method and system are unique in that it is different from other known processes or solutions. More specifically, it is a (1) new and novel process for grading and harvesting hemp micro green materials; (2) tailored to the specific agricultural demands of the hemp plant; and (3) is scalable and reproducible while being more efficient than existing methods of manufacturing similar products (e.g. sprouted seed cake). In one embodiment, the process in FIG. 3 may proceed to step 306 of processing all hemp microgreens to be juiced with proper equipment and water, wherein not in excess of 200 ml per kilo of fresh greens can be added to aid in the blending and liquification of the greens. Further, as part of the processing, step 308 includes freeze-drying high grade juice at −21° C. for at least 12 hours, until completely desiccated and/or blending low grade juice with appropriate emulsifier in a ratio of 40:60 liquid to starch. The process may terminate at step 312.

In another embodiment of the present invention and with reference to FIG. 4, a method of grading and processing hemp microgreens into a consumable hemp microgreen desiccant. In said method, the process may begin at step 400 and immediately proceed to step 402 of screening a plurality of hemp seeds for a predetermined manufacturing use that is based on a plurality of quantitative seed characteristics, including a fatty acid profile, a cannabinoid and nutrient panel, and a projected detectable quantity of THC or CBD at any point during a plant's life cycle having a potential for a cannabinoid synthesis. In one embodiment, the detectible quantity of THC or CBD at any point during a plant's life cycle is 0.001%. This screening is preferably done manually but may also include specific technology operably configured to screen based on the above-described characteristics. The fatty acid profile is a chemical test done analytically and is typically done by an outside vendor not associated with the separation, cultivation and secondary screen steps discussed more further herein. In some embodiments, step 402 may include the projected detectible quantity of THC or CBD being genetically screened to exclude any of the plurality of hemp seeds having the potential for the cannabinoid synthesis over the detectible quantity of THC or CBD at any point during the plant's life cycle.

Next, the process may include step 404 of separating the plurality of hemp seeds into a first separated plurality of hemp seeds and a second separated plurality of hemp seeds based on at least one of a plurality of organoleptic seed characteristics predicated on a standard for manufacturing high-grade hemp microgreens. Some exemplary organoleptic seed characteristics include seed size, seed smell, seed taste, seed shape, and seed shell integrity. Similarly, the standard for manufacturing high-grade hemp microgreens may include having a 4-6 cm green or red stem with symmetrical leaves and of an even color without blemishes. The seed hull should have completely fallen from the sprout and only four leaves (two true and two cotyledons) should be visible. Low-grade hemp microgreens may be based on a microgreens non-qualification as high-grade and/or may be based on criteria that includes imperfections which lower the grade of the sprout, wherein any single criteria renders a sprout low grade and may include: (1) retention of seed or husk in part or whole, or residue from the seed and husk, (2) improper opening manifested as asymmetrical, uneven growth or unfurled and misshapen leaves (cotyledons and true leaves)—sprouts with two sets of partially mature or mature true leaves are also considered low grade sprouts, but buds are okay, (3) nutrient deficiencies, specifically, yellowing in the leaves or excessive whiteness in the stems, (4) stem length in excess of 6 cm or that is curved or bent, or (5) any high grade micros damaged during harvest or handling become low grade. Also in one embodiment, the plurality of hemp seeds are cleaned based on the categorized manufacturing use. For example, the plurality of hemp seeds would not be bleached if utilized for human consumption.

Next, the process may include the step 406 of cultivating a plurality of hemp microgreens with the first separated plurality of hemp seeds. Further, the process includes step 408 of doing a secondary screening Specifically, step 408 includes screening the plurality of hemp microgreens based on organoleptic characteristics of the plurality of hemp microgreens and quantitative characteristics that includes a fatty acid profile and a cannabinoid and nutrient panel that measures for a total detectible quantity of cannabinoids, including THC or CBD, that are both cross referenced and/or confirmed (reconciled for differences) with the fatty acid profile and the projected detectible quantity of THC or CBD ascertained in the screening of the plurality of hemp seeds to maintain grading standards. In some embodiments, step 408 includes screening the plurality of hemp microgreens based on a quantitative characteristic that includes detecting the presence of mycotoxins and, when detected, not including said detected hemp microgreens with mycotoxins in the first and second separated plurality of hemp seeds. Said another way, any microgreens detected with mycotoxins are completely discarded and not used.

In one embodiment, some organoleptic characteristics include hemp microgreens grown for 9 to 12 days and having a visual description that includes stemmy green sprout(s) (5-10 cm) with cotyledons, one pair of true leaves (2 cm) with a single point, and some budding for new growth. Slight fuzziness on true leaves, sawed. Further, the hemp microgreens may include thin whitish green or red stem(s), (2-3 mm) and thinner tap root (<1 mm) with some ancillary root expression up to 15 cm in length. Some sensory attributes include slight fuzziness on true leaves and crisp and slight fibrous stem, snappable. The smell of the hemp microgreens may be "grassy" and the taste may be bitter and slightly peppery, with a faint citrus finish. The mouthfeel would be similar to oregano and taste comparable to arugula micros.

Next. the process may proceed to step 410 of separating the plurality of hemp microgreens into a first plurality of high-grade hemp microgreens based on the standard for manufacturing high-grade hemp microgreens and a second plurality of low-grade hemp microgreens. The low-grade hemp microgreens may also be described as those hemp microgreens that are basically microgreens that do not meet the standard of high-quality hemp microgreens. The separating step is done visually by the user. From a quality control standpoint, a first examination or pass includes the tray(s) of hemp microgreens being screened for a rough ratio of high and low grade with a visual inspection. Tray(s)s with a ratio of 70:30 (High to Low Grade) or greater (meaning a higher percentage of high grade micros) will be separated for trim harvesting. The remaining trays will be pulled and harvested before being cleaned. A second examination or pass includes the tray(s) separated for trim harvesting are trimmed, during which point low grade micros will be separated. High grade microgreens will be cleaned and given a final quality assessment while being packaged. Hemp microgreens on the tray(s) will be plucked in a manner that maximizes root retention and rinsed before being left to air dry, wherein the substrate will be cleaned in a similar manner and prepared for processing.

Continuing further, step 412 includes packaging the first plurality of high-grade hemp microgreens into a physical container for fresh sale, i.e., within the window of perishability, e.g., five days after harvest. Said another way, the packaging step 412 may include packaging the plurality of hemp microgreens into either a high-grade hemp microgreens or a low-grade hemp microgreens. High-grade hemp microgreens are sold and low-grade are used in processing. Separating may also be included in the term harvesting and the hemp microgreens may be graded while they are harvested. In preferred embodiments, the first plurality of high-grade hemp microgreens are placed in a sealable container.

Next, the process includes step 414 of processing the second plurality of low-grade hemp microgreens into a consumable hemp microgreen desiccant. The processing may include, for example, a dehydrator or oven and a milling machine, i.e., a thereto treatment and some type of kinetic process. In one embodiment, the process includes blending the consumable hemp microgreen desiccant and a hemp seed powder generated from the second separated plurality of hemp seeds to generate a homogenous consumable ingredient. When blended, the consumable hemp microgreen desiccant and the hemp seed powder should be have at least similar particle size and be of a consistent density. In one embodiment, the second separated plurality of hemp seeds, i.e., low grade seeds, are smashed into the hemp seed powder and blended into the homogenous consumable ingredient. Before smashed, the second separated plurality of hemp seeds may be heat-treated before smashing into the hemp seed powder.

In one embodiment, the process includes separating the plurality of hemp seeds having a seed size of approximately 0.3 mm and ascertaining a seed size standard deviation for categorizing a manufacturing use of the plurality of hemp seeds. The 0.3 mm is preferably, based on testing, the best size for growing hemp microgreens.

In one embodiment of the present invention, the plurality of hemp seeds are separated into a third separated plurality of hemp seeds based on the manufacturing use. Further, the plurality of hemp seeds may also be randomly screened at a desired time or event interval for a predetermined manufacturing use.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A method of grading and processing hemp microgreens into a consumable hemp microgreen desiccant comprising the steps of:
   screening a plurality of hemp seeds for a predetermined manufacturing use that is based on a plurality of quantitative seed characteristics including a fatty acid profile, a cannabinoid and nutrient panel, and a projected detectible quantity of THC or CBD at any point during a plant's life cycle having a potential for a cannabinoid synthesis;
   separating the plurality of hemp seeds into a first separated plurality of hemp seeds and a second separated plurality of hemp seeds based on at least one of a plurality of organoleptic seed characteristics predicated on a standard for manufacturing high-grade hemp microgreens;
   cultivating a plurality of hemp microgreens with the first separated plurality of hemp seeds;
   screening the plurality of hemp microgreens based on organoleptic characteristics of the plurality of hemp microgreens and quantitative characteristics including a fatty acid profile and a cannabinoid and nutrient panel that measures for a total detectible quantity of cannabinoids, including THC or CBD, that are both cross referenced with the fatty acid profile and the projected detectible quantity of THC or CBD ascertained in the screening of the plurality of hemp seeds to maintain grading standards;
   separating the plurality of hemp microgreens into a first plurality of high-grade hemp microgreens based on the standard for manufacturing high-grade hemp microgreens and a second plurality of low-grade hemp microgreens;
   packaging the first plurality of high-grade hemp microgreens into a container for fresh sale; and
   processing the second plurality of low-grade hemp microgreens into a consumable hemp microgreen desiccant.

2. The method according to claim 1, wherein:
   the projected detectible quantity of THC or CBD is genetically screened to exclude any of the plurality of hemp seeds having the potential for the cannabinoid synthesis over the detectible quantity of THC or CBD at any point during the plant's life cycle.

3. The method according to claim 1, further comprising:
   blending the consumable hemp microgreen desiccant and a hemp seed powder generated from the second separated plurality of hemp seeds to generate a homogenous consumable ingredient.

4. The method according to claim 3, further comprising:
   smashing the second separated plurality of hemp seeds into the hemp seed powder blended into the homogenous consumable ingredient.

5. The method according to claim 4, further comprising:
   heat-treating the second separated plurality of hemp seeds before smashing into the hemp seed powder.

6. The method according to claim 4, further comprising:
   screening the plurality of hemp microgreens based on a quantitative characteristic that includes detecting the presence of mycotoxins and, when detected, not including said detected hemp microgreens with mycotoxins in the first and second separated plurality of hemp seeds.

7. The method according to claim 1, wherein the plurality of organoleptic seed characteristics further comprises:

a seed size, a seed smell, a seed taste, a seed shape, and a seed shell integrity.

8. The method according to claim 1, further comprising:

separating the plurality of hemp seeds having a seed size of approximately 0.3 mm; and ascertaining a seed size standard deviation for categorizing a manufacturing use of the plurality of hemp seeds.

9. The method according to claim 8, further comprising:

cleaning the plurality of hemp seeds based on the categorized manufacturing use.

10. The method according to claim 1, further comprising:

separating a plurality of hemp seeds into a third separated plurality of hemp seeds based on the manufacturing use.

11. The method according to claim 1, further comprising:

randomly screening the plurality of hemp seeds for a predetermined manufacturing use.

12. The method according to claim 1, wherein:

the detectible quantity of THC or CBD at any point during a plant's life cycle is 0.001%.

* * * * *